United States Patent
Knauf et al.

(10) Patent No.: US 6,495,577 B2
(45) Date of Patent: Dec. 17, 2002

(54) PESTICIDAL COMPOSITION

(75) Inventors: Werner Knauf, Liederbach (DE); Gerald Michel Yvon Huart, Ecully (FR); Kay Christoph Grosser, Neumühlstrasse (DE)

(73) Assignee: Aventis CropScience GmbH, Frankfurt am Main (DE)

( * ) Notice: Subject to any disclaimer, the term of this patent is extended or adjusted under 35 U.S.C. 154(b) by 0 days.

(21) Appl. No.: 09/970,615

(22) Filed: Oct. 4, 2001

(65) Prior Publication Data

US 2002/0061928 A1 May 23, 2002

(30) Foreign Application Priority Data

Oct. 7, 2000 (EP) .............................................. 00121924

(51) Int. Cl.$^7$ .......................... A01N 43/40; A01N 37/34
(52) U.S. Cl. ........................................ 514/357; 514/521
(58) Field of Search .................................. 514/357, 521

(56) References Cited

U.S. PATENT DOCUMENTS 5,880,142 A  3/1999  Otsu et al. ................... 514/357

FOREIGN PATENT DOCUMENTS

FR    2784011    4/2000

OTHER PUBLICATIONS

Tomlin, The Pesticide Manual, eleventh edition, 1997, pp. 9, 10 and 344–346.*

* cited by examiner

Primary Examiner—Allen J. Robinson
(74) Attorney, Agent, or Firm—Frommer Lawrence & Haug LLP

(57) ABSTRACT

Pesticidal compositions comprising deltamethrin and acetamiprid.

4 Claims, No Drawings

PESTICIDAL COMPOSITION

This invention relates to pesticidal compositions containing acetamiprid.

In FR 2784011 there are described mixtures of pyrethroids with a chloronicotinyl insecticide, such as imidacloprid, acetamiprid or nitenpyram. The only pyrethroid specifically disclosed is cypermethrin. U.S. Pat. No. 5,880,142 describes mixtures of chloronicotinyl insecticides and pyrethroids for termite control and discloses a mixture of acetamiprid and cyfluthrin.

We have now found that a mixture of another pyrethroid, deltamethrin, with acetamiprid has advantageous properties over the individual components and that synergism is often demonstrated.

Accordingly the present invention provides a pesticidal composition comprising
a) deltamethrin and
b) acetamiprid.

Deltamethrin is the common name for (S)-α-cyano-3-phenoxybenzyl (1R,3R)-3-(2,2-dibromvinyl)-2,2-dimethylcyclopropanecarboxylate and acetamiprid is the common name for E-$N^1$-[(6-chloro-3-pyridylmethyl)]-$N^2$-cyano-$N^1$-methylacetamidine.

The ratios of the deltamethrin to acetamiprid vary over a wide range but are usually in the range 5:1 to 1:10, especially 1:1 to 1:5.

In addition, other pesticides may be employed in conjunction with the active ingredients described above providing they do not adversely affect the interaction between the components a) and b). For example it is sometimes useful to include additional insecticides or acaricides to extend the range of activity in order to control a wider spectrum of pests.

The combination is also useful in overcoming reduced sensitivity by a pest to either of the individual components.

The compositions of the invention are active against a wide range of pests, especially sucking pests such as Thrips spp., e.g. *Ttabaci* and *Tpalmi*, Homoptera, including aphids such as *Megoura viciae* and plant hoppers,such as *Nilaparvata lugens* and *Nephotettix cincticeps*, whiteflies, such as *Trialeurodes vaporarorum* and *Bemisia tabaci*, and Psylla spp., Heteroptera. e.g. bed bugs such as *Cimex lectularius*, and capsids, Lepidoptera, including Spodoptera spp, eg *S.littoralis*, Heliothis spp., eg *H. armigera* and *H. viriscens*, and *Pieris brassicae*; Diptera, including *Musca domestica, Ceratitis capitata, Erioischia brassicae, Lucilia sericata* and *Aedes aegypti*; Coleoptera, including *Phaedon cochleariae, Anthonomus grandis* and corn rootworms (Diabrotica spp. e.g. *D. undecimpunctata*); Orthoptera, including cockroaches, such as *Blattella germanica*; ticks, e.g. *Boophilus microplus*; lice, including *Damalinia bovis* and *Linognathus vituli*; as well as spider mites such as *Tetranychus urticae* and *Panonychus ulmi*.

The compositions of the invention may be employed in many forms and are often most conveniently prepared in aqueous form immediately prior to use. One method of preparing such a composition is referred to as "tank mixing" in which the ingredients in their commercially available form are mixed together by the user in a quantity of water.

In addition to tank mixing immediately prior to use the compositions containing deltamethrin and acetamiprid may be formulated into a more concentrated primary composition which is diluted with water or other diluent before use. Such compositions may comprise a surface active agent in addition to the active ingredients and examples of such compositions are as follows.

It can be a dispersible solution which comprises the active ingredients dissolved in a water-miscible solvent with the addition of a dispersing agent. Alternatively it can comprise the ingredients in the form of a finely ground powder in association with a dispersing agent and intimately mixed with water to give a paste or cream which can if desired be added to an emulsion of oil in water to give a dispersion of active ingredients in an aqueous oil emulsion.

An emulsifiable concentrate comprises the active ingredient dissolved in a water-immiscible solvent which is formed into an emulsion with water in the presence of an emulsifying agent.

A granular solid comprises the active ingredients associated with powder diluents such as kaolin, which mixture is granulated by known methods. Alternatively it comprises the active ingredients adsorbed or absorbed on a pre-granular diluent, for example Fuller's earth, attapulgite or limestone grit.

A dispersible or wettable powder usually comprises the active ingredients in admixture with a suitable surfactant and an inert powder diluent such as china clay.

Another suitable concentrate is a flowable suspension concentrate which is formed by grinding the active ingredients with water, a wetting agent and a suspending agent.

In some circumstances it may be desirable to combine two types of formulation e.g. one of the components is present in an emulsifiable concentrate and the second components is dispersed as a powder in this concentrate.

The concentrate of the active ingredients (when used as the sole active components) in a composition for direct application to the crop by conventional ground methods is preferably within the range of 0.001 to 10 per cent by weight of the composition, especially 0.005 to 5 per cent by weight, but more concentrated compositions containing up to 40 per cent may be desirable in the case of aerial sprays.

The invention thus includes a method for controlling a pest, especially an arthropod pest, e.g. an insect pest or an Acarina pest, which comprises applying to the pest or its locus, deltamethrin and acetamiprid either together or in sequence.

Further there is provided the use of a mixture comprising deltamethrin and acetamiprid for controlling pests.

The disclosures in European patent application No. 00121924.5 from which this application claims priority, and in the abstract accompanying this application are incorporated herein by reference.

The invention is illustrated in the following Example which describe experiments in which a synergistic effect was observed. The desired concentration of the active ingredients was achieved by diluting, with water, the commercially available 25% by volume emulsifiable concentrate of deltamethrin and 20% by weight water soluble powder of acetamiprid, each of which contained conventional surfactants.

EXAMPLE

Two plants of two week old French beans (*Phaseolus vulgaris*) were infested with adult whitefly (*Trialeurodes vaporariorum*) for oviposition in a closed chamber. After 48 hours, the adults were blown off the plants so that only the eggs stayed at the surface of the leaves. The plants were placed in a greenhouse for 7 days to complete the development of the eggs to the larval stage L 1/2. The plants were then sprayed with the individual compounds and mixtures of the two, by hand with a spray gun, until complete coverage of the plant surfaces with the spray liquid was obtained. The plants were then placed in the greenhouse for a further 10 days. Two replicates of each test was carried. The mortality of the nymphs of *Trialeurodes vaporadorum* was estimated 10 days after application and the average of the two replicates calculated.

To indicate the existence of synergism between the active components, the results were treated in the manner described by Colby S. R., "Calculating Synergistic and Antagonistic Responses of Herbicide Combinations," *Weeds*, 1967, 15, 20–22. In this method, the "expected" percent control, E, of the combination is given by the equation:

$$E = X + Y - \frac{XY}{100}$$

in which

X=the percentage of control with substance A at a given rate (p),

Y=the percentage of control with substance B at a given rate (q), and

E=expected control by A+B at a rate p+q.

If the observed control of the mixture is greater than E the results indicate synergism.

The results were as follows:

| deltamethrin (D) (ppm) | acetamiprid (A) (ppm) | mortality in (%) | Expected mortality (E) according to Colby |
|---|---|---|---|
| 1 | — | 73,75 | |
| 0,6 | — | 47,5 | |
| 0,33 | — | 47,5 | |
| 0,2 | — | 36,25 | |
| 0,1 | — | 25 | |
| 0,06 | — | 15 | |
| 0,033 | — | 8,75 | |
| 0,02 | — | 2,5 | |
| 0,01 | — | 0,75 | |
| 0,006 | — | 0 | |
| — | 3 | 56,25 | |
| — | 1 | 23,75 | |
| — | 0,3 | 7,5 | |
| — | 0,1 | 1,25 | |
| — | 0,03 | 0 | |
| 1 | 3 | 82,5 | 88,5 |
| 0,33 | 1 | 82,5 | 60 |
| 0,1 | 0,3 | 55 | 30,6 |
| 0,033 | 0,1 | 35 | 9,9 |
| 0,01 | 0,03 | 8,75 | 0,75 |

| deltamethrin (D) (ppm) | acetamiprid (A) (ppm) | mortality in (%) | Expected mortality (E) according to Colby |
|---|---|---|---|
| 0,6 | 3 | 93,75 | 77,0 |
| 0,2 | 1 | 63,75 | 51,4 |
| 0,06 | 0,3 | 33,75 | 21,4 |
| 0,02 | 0,1 | 10,5 | 3,7 |
| 0,006 | 0,03 | 2,25 | 0 |

The $LC_{50}$ in ppm of the mixtures was calculated and compared with the expected $LC_{50}$ from the expected mortalities according to Colby.

The results were as follows:

| Ratio of D:A | $LC_{50}$ (ppm) | $LC_{50}$ (ppm), expected according to Colby |
|---|---|---|
| 1:3 | 0,261 | 0,631 |
| 1:5 | 0,523 | 1,000 |

What is claimed is:

1. A pesticidal composition, comprising:

a) deltamethrin; and b) acetamiprid, wherein the synergistic ratio of deltamethrin to acetamiprid is in the range of from 5:1 to 1:10.

2. The composition according to claim 1, wherein the ratio of deltamethrin to acetamiprid is in the range of from 1:1 to 1:5.

3. A method for controlling a pest, comprising the step of applying to the pest or its locus, deltamethrin and acetamiprid, either together or in sequence, wherein the synergistic ratio of deltamethrin to acetamiprid is in the range of from 5:1 to 1:10.

4. A method for controlling a pest, comprising the step of applying to the pest or its locus, deltamethrin and acetamiprid, either together or in sequence, wherein the synergistic ratio of deltamethrin to acetamiprid is in the range of from 1:1 to 1:5.

* * * * *